US005738987A

United States Patent [19]

Milliman

[11] Patent Number: 5,738,987
[45] Date of Patent: Apr. 14, 1998

[54] 16S RIBOSOMAL NUCLEIC ACID PROBES TO *STREPTOCOCCUS PNEUMONIAE*

[75] Inventor: Curt L. Milliman, St. Louis, Mo.

[73] Assignee: Gen-Probe Incorporated, San Diego, Calif.

[21] Appl. No.: 427,712

[22] Filed: Apr. 21, 1995

Related U.S. Application Data

[63] Continuation of Ser. No. 118,579, Sep. 9, 1993, abandoned, which is a continuation of Ser. No. 753,361, Sep. 4, 1991, abandoned.

[51] Int. Cl.$^6$ ............... C12Q 1/68; C07H 21/04; C12N 15/11
[52] U.S. Cl. ............. 435/6; 536/24.32; 536/237; 935/77; 935/78
[58] Field of Search .............. 435/6; 536/24.32, 536/23.1, 23.7; 935/77, 78

[56] References Cited

U.S. PATENT DOCUMENTS

| 4,689,295 | 8/1987 | Taber et al. ............... 435/6 |
| 4,851,330 | 7/1989 | Kohne ........................ 435/6 |
| 5,030,557 | 7/1991 | Hogan et al. ............... 435/6 |
| 5,232,831 | 8/1993 | Milliman et al. ........... 435/6 |
| 5,288,611 | 2/1994 | Kohne ........................ 435/6 |

FOREIGN PATENT DOCUMENTS

| A-31387/84 | 7/1985 | Australia. |
| 0155359 | 3/1982 | European Pat. Off.. |
| WO 8301073 | 3/1983 | WIPO. |
| WO 84/02721 | 9/1984 | WIPO. |
| WO88/03957 | 11/1988 | WIPO. |

OTHER PUBLICATIONS

Lane et al., v. 82 Proc. Natl. Acad. Sci. USA p. 6955, 1985.
Rogers et al., v. 82 Proc. Natl. Acad. Sci. USA p. 1160, 1985.
Brosius et al., v.75 Proc. Natl. Acad. Sci., USA p. 4801, 1978.
Brosius et al., v.77 Proc. Natl. Acad. Sci., USA p. 201, 1980.
Weisburg et al., 1. 167 Journal of Bacteriology p. 570, 1986.
Kohne, American Clinical Products Review, Nov. 1986.
Brenner, in Impact of Biotechnology on Microbial Detection, Estimation, and Characterization, B. Swaminathan et al., eds. Dekker, Inc. New York.
Razin, v. 49 Microbiological Reviews p. 419, 1985.
Crosa et al., v. 83 Journal of General Microbiology p. 271, 1974.
V.9 Clinical Microbiology Newsletter p. 90, 1987.
Stahl, v. 4 Biotechnology p. 623, 1986.
Brenner et al., vol. 90 Annals of Internal Medicine p. 656, 1979.
Ludwig and Stackebrandt, v. 135 Archives of Microbiology p. 45, 1983.
Brenner et al., v. 1 Current Microbiology 71, p. 1978.
Kohne et al., In Thornsbury et al., *Legionella* Proceedings of the Second International Symposium, American Society for Microbiology, Washington, p. 107.

Taber et al., U.S. Patent 4,689,295, Aug. 25, 1987.
Webster WO 8301073, Mar., 1983.
Gen-Probe Partners, WO 84/02721, Sep. 1984.
Webster, EPA 0155359, Mar., 1982.
Hogan et al., PCT WO88/03957, Nov. 1988.
Carrico et al., AU-A-31387/84, Jul. 1985.
Brenner, Bergey's Manual of Systemic Bacteriology, v. 1, (1984) p. 238.
Brenner et al., International Journal of Systematic Bacteriology, 1985, vol. 35, p. 50.
Grimont et al., 21 J. Clin. Microbiol. 431, 1985.
Brenner et al., International Journal SB v. 30, 1980, p. 236
1 Bergy's Manual of Systematic Bacteriology p. 160, 1984.
Festl et al., v. 52 Applied and Environmental Microbiology p. 1190, 1986.
Carbon et al., v. 9 Nucleic Acid Research p. 2325, 1981.
Colwell et al., v. 24 International Journal of Systematic Bacteriology p. 422, 1974.
Brenner, v. 23 International Journal of Systematic Bacteriology p. 298, 1973.
Brenner, v. 1 Bergy's Manual of Systematic Bacteriology 408, 1984.
McCarroll et al., 22 Biochemistry 5858, 1983.
Veldman et al., v. 9 Nucleic Acids Research p. 6935, 1981.
Kilpper-Balz et al., vol. 7 Current Microbiology p. 245, 1982.
Kilpper-Balz and Schleifer, vol. 10 FEMS Microbiology Letters p. 357, 1981.
Schleifer and Kilpper-Balz, vol. 34 International Journal of Systematic Bacteriology p. 31, 1984.
Harvey and Greenwood, v. 33 International Journal of Systematic Bacteriology p. 275, 1983.
Lau et al., v. 447 System Appl. Microbiol. Immunol. Scand. Sect. B p. 201, 1983.
Baess v. 91 Adv. Path. Microbiol. Immunol. Scand. Sect. B p. 201, 1983.
Imaeda, v. 35 International Journal of Systematic Bacteriology p. 147, 1985.
Baess and Bentzon, v. 86 Acta Pat. Microbiol. Scand. Sect. B p.71, 1978.
Drake et al., v. 25 Journal Clinical Microbiology, 1987 p. 210.
Stackebrandt and Schleifer, eds. in Biological Biochemical, Biochemical Aspects of Actinomycetes p. 485, 1984.
Goodfellow and Minnikin, In The Mycobacteria, Kubica and Wayne, eds. Dekker, (1984). N.Y. New York.
Mordarski et al., v. 118 Journal of General Microbiology, p. 313, 1980.
Goodfellow and Wayne, in v. 1 The Biology of the *Mycobacteria* p. 476, 1982.
Baess, v. 90 Acta Path. Microbiol. Immunol. Scand. Sect. B. p. 371, 1982.

(List continued on next page.)

*Primary Examiner*—Lisa B. Arthur
*Attorney, Agent, or Firm*—Lyon & Lyon LLP

[57] ABSTRACT

16S ribosomal nucleic acid hybridization assay probes specific for *Streptococcus pneumoniae* and no other Streptococcus species.

24 Claims, No Drawings

OTHER PUBLICATIONS

Bradley, v. 113 Journal of Bacteriology p. 645, 1973.
Rogers et al., v. 82 Proc. Natl. Acad. Sci. USA p. 1160, 1985.
Yogev and Razin, v. 36 International Journal of Systematic Bacteriology p. 426, 1986.
Razin et al., v. 135 Ann. Microbiol. p. 9,1984.
Gobel et al., v. 133 Journal of General Microbiology p. 1969, 1987.
Gobel, v. 226 Science p. 1211, 1984.
Razin, v. 49 Microbiol. Rev. p. 437, 1985.
Jones and Collins, v. 1 Bergy's Manual of Systematic Bacteriology p. 1261, 1986.
Boddinghaus et al., v. 28 J. Clin. Micro p. 1751, 1990.
Rogall et al., v. 40 Int. J. Sys. Bact. p. 323, 1990.
Rogall et al., v. 136 J. Gen. Micro. p. 1915, 1990.
Stahl and Urbance v. 172 J. Bact. p. 116, 1990.
Kilian v. 93 J. Gen. Micro. p. 9, 1976.
Musser et al., v. 52 Inf. Imm. p. 183, 1983.
Malouin et al., v. 26 J. Clin. Micro. p. 2132, 1988.
Bacot, C.M. et al. (Jul. 1991) Journal of Bacteriology, vol. 173, No. 13 pp. 4234–4236.
Rappaport, T. et al (1988) Journal of Clinical Microbiology, vol. 26 (7), pp. 1335–1338.
Kohne, D.E. (Nov. 1986) American Clincial Proceedings, "Application of DNA probe tests to the diagnosis of infectious disease", Farfield, CT.
Barry, T. et al. (Mar. 1990) BioTechnology, vol. 8: 233–236.
Whiley et al. (1990) FEMS Microbiol. Lett 68 (1990) 115–122.
Bentley et al. (Oct. 1991) Int. J. Systemic Bacteriol. 41(4):487–494.

SEQUENCE LISTING ( 1 ) GENERAL INFORMATION:

( i i i ) NUMBER OF SEQUENCES: 6

( 2 ) INFORMATION FOR SEQ ID NO: 1:

( i ) SEQUENCE CHARACTERISTICS:
( A ) LENGTH: 22
( B ) TYPE: nucleic acid
( C ) STRANDEDNESS: single
( D ) TOPOLOGY: linear ( i i ) SEQUENCE DESCRIPTION: SEQ ID NO: 1:

CAAAGCCTAC TATGGTTAAG CC          22

( 2 ) INFORMATION FOR SEQ ID NO: 2:

( i ) SEQUENCE CHARACTERISTICS:
( A ) LENGTH: 37
( B ) TYPE: nucleic acid
( C ) STRANDEDNESS: single
( D ) TOPOLOGY: linear ( i i ) SEQUENCE DESCRIPTION: SEQ ID NO: 2:

ACAGCCTTTA ACTTCAGACT TATCTAACCG CCTGCGC          37

( 2 ) INFORMATION FOR SEQ ID NO: 3:

( i ) SEQUENCE CHARACTERISTICS:
( A ) LENGTH: 32
( B ) TYPE: nucleic acid
( C ) STRANDEDNESS: single
( D ) TOPOLOGY: linear ( i i ) SEQUENCE DESCRIPTION: SEQ ID NO: 3:

```
TCTCCCCTCT TGCACTCAAG TTAAACAGTT TC                                      32
```

( 2 ) INFORMATION FOR SEQ ID NO: 4:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 4:

```
GGCTTAACCA TAGTAGGCTT TG                                                 22
```

( 2 ) INFORMATION FOR SEQ ID NO: 5:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 5:

```
GGCUUAACCA UAGUAGGCUU UG                                                 22
```

( 2 ) INFORMATION FOR SEQ ID NO: 6:

( i ) SEQUENCE CHARACTERISTICS:
        ( A ) LENGTH: 22
        ( B ) TYPE: nucleic acid
        ( C ) STRANDEDNESS: single
        ( D ) TOPOLOGY: linear ( i i ) SEQUENCE DESCRIPTION: SEQ ID NO: 6:

```
CAAAGCCUAC UAUGGUUAAG CC                                                 22
```

16S RIBOSOMAL NUCLEIC ACID PROBES TO *STREPTOCOCCUS PNEUMONIAE*

This application is a continuation of U.S. Ser. No. 08/118,579, filed Sep. 9, 1993, now abandoned, which is a continuation of U.S. Ser. No. 07/753,361, filed Sep. 4, 1991, now abandoned.

FIELD OF THE INVENTION

The inventions described and claimed herein relate to the design and construction of nucleic acid probes to *Streptococcus pneumoniae* which are capable of detecting the organism in test samples of, e.g., sputum, urine, blood and tissue sections, food, soil and water.

BACKGROUND OF THE INVENTION

Two single strands of deoxyribo- ("DNA") or ribo- ("RNA") nucleic acid, formed from nucleotides (including the bases adenine (A), cytosine (C), thymidine (T), guanine (G), uracil (U), or inosine (I)), may associate ("hybridize") to form a double stranded structure in which the two strands are held together by hydrogen bonds between pairs of complementary bases. Generally, A is hydrogen bonded to T or U, while G is hydrogen bonded to C. At any point along the chain, therefore, one may find the classical base pairs AT or AU, TA or UA, GC, or CG. One may also find AG, GU and other "wobble" or mismatched base pairs.

When a first single strand of nucleic acid contains sufficient contiguous complementary bases to a second, and those two strands are brought together under conditions which will promote their hybridization, double stranded nucleic acid will result. Under appropriate conditions, DNA/DNA, RNA/DNA, or RNA/RNA hybrids may be formed.

A probe is generally a single stranded nucleic acid sequence which is complementary to some degree to a nucleic acid sequence sought to be detected ("target sequence"). It may be labelled with a detectable moiety such as a radioisotope, antigen or chemiluminescent moiety. A background description of the use of nucleic acid hybridization as a procedure for the detection of particular nucleic acid sequences is described by Kohne, U.S. Pat. No. 4,851, 330, and Hogan et al., EPO Patent Application No. PCT/US87/03009, entitled "Nucleic Acid Probes for Detection and/Or Quantitation of Non-Viral Organisms."

Hogan et al., supra, also describes methods for determining the presence of RNA-containing organisms in a sample which might contain such organisms. These methods require probes sufficiently complementary to hybridize to the ribosomal RNA (rRNA) of one or more non-viral organisms or groups of non-viral organisms. The mixture is then incubated under specified hybridization conditions, and assayed for hybridization of the probe and any test sample rRNA.

Hogan et al. also describes probes which detect only specifically targeted rRNA subunit subsequences in particular organisms or groups of organisms in a sample, even in the presence of many non-related organisms, or in the presence of the closest known phylogenetic neighbors. Specific examples of hybridization assay probes are provided for *Mycobacterium avium*, *Mycobacterium intracellulare*, *Mycobacterium tuberculosis*, *Mycobacterium africanum*, *Mycobacterium bovis*, *Mycobacterium microti*, the genus Mycobacterium, *Mycoplasma pneumoniae*, the genus Legionella, *Chlamydia trachomatis*, the genus Campylobacter, Enterococcus, the genus Pseudomonas group I, *Enterobacter cloacae*, *Proteus mirabilis*, the genus Salmonella, *Escherichia coli*, bacteria, fungi, and *Neisseria gonorrhoea*. Such probe sequences do not cross react with nucleic acids from the groups listed above, or any other bacterial species or infectious agent, under appropriate hybridization stringency conditions.

SUMMARY OF THE INVENTION

*Streptococcus pneumoniae* (Pneumococcus) is the leading cause of community acquired bacterial pneumonia in the United States, occurring in approximately one half million cases per year, with a complication and death rate of about 5% (Facklam and Carey, Streptococci and aerococci, Manual of Clinical Microbiology, Fourth Edition. eds. Lennette et al. American Society for Microbiology, Washington, D.C. 154–175, 1985, and Klainer, Pneumococcal pneumonia, Seminars in Infectious Disease V. First Edition Weinstein and Fields Thieme-Stratton Inc. New York, N.Y., 3–9, 1983). *Streptococcus pneumoniae* is the leading cause of otitis media and bacteremia in infants and children and is a common cause of meningitis, and has been isolated from patients with conjunctivitis, sinusitis, mastoiditis, pericarditis, occult bacteremia, arthritis and endocarditis.

Presumptive identification of *S. pneumoniae* is made by traditional physiological and biochemical methods. These include colony morphology, gram stain, catalase reaction, alpha hemolytic activity on 5% sheep blood agar, optochin susceptibility and bile solubility. More than 80 serotypes have been identified, based on capsular polysaccharides. The Quellung test, based on apparent capsular swelling in response to treatment with antisera to these polysaccharides is another means of identification. All these tests are subjective, and no one by itself provides unequivocal identification of *Streptococcus pneumoniae*.

Thus, in a first aspect, the invention features a hybridization assay probe able to distinguish *Streptococcus pneumoniae* from other Streptococcus species.

In preferred embodiments, the probe is complementary to rRNA or rDNA, e.g., a variable region of rRNA; at least 50% of the nucleotides in the oligonucleotide probe are able to hybridize to a contiguous series of bases in at least one variable region of ribosomal nucleic acid in *Streptococcus pneumoniae*; the probe is a nucleotide polymer able to hybridize to the rRNA of the species *Streptococcus pneumoniae* in the region corresponding to bases 616–638 of *E. coli* 16S rRNA, or a nucleotide polymer complementary thereto; and the oligonucleotide comprises, consists essentially of, or consists of the sequence (SEQ. ID. NO.: 1) CAAAGCCTACTATGGTTAAGCC or oligonucleotides complementary thereto, with or without a helper probe, as described below.

By "consists essentially of" is meant that the probe is provided as a purified nucleic acid which hybridizes under stringent hybridizing conditions with the desired organism and not with other related organisms. Such a probe may be linked to other nucleic acids which do not affect such hybridization. Generally, it is preferred that the probe be of between 15 and 100 (most preferably between 20 and 50) bases in size. It may, however, be provided in a vector.

In related aspects, the invention features a nucleotide polymer able to hybridize to the above oligonucleotides, a nucleic acid hybrid formed with the above oligonucleotides, and a nucleic acid sequence substantially complementary thereto.

The probes of this invention offer a rapid, non-subjective method of identification and quantitation of a bacterial colony for the presence of specific rRNA sequences unique to all strains of *Streptococcus pneumoniae*.

DESCRIPTION OF THE PREFERRED EMBODIMENTS

Probes

We have discovered DNA probes complementary to a particular rRNA sequence obtained from *Streptococcus pneumoniae*. Furthermore, we have successfully used those probes in a specific assay for the detection of *Streptococcus pneumoniae*, distinguishing *S. pneumoniae* from its known and presumably most closely related taxonomic or phylogenetic neighbors.

With the exception of viruses, all prokaryotic organisms contain rRNA genes encoding 5S rRNA, 16S rRNA and a larger rRNA molecule known as 23S rRNA. Using methods known to those skilled in the art, variable regions of rRNA sequences from the 16S rRNA of *Streptococcus pneumoniae* were identified as described below. Other such sequences can be identified using equivalent techniques. These methods include partially or fully sequencing the rRNA of *Streptococcus pneumoniae* and closely related phylogenetic neighbors, aligning the sequences to reveal areas of maximum homology, and examining the alignment for regions with sequence variation. The examples provided below are thus not limiting in this invention.

With respect to sequencing, complementary oligonucleotide primers of about 10–100 bases in length were hybridized to conserved regions in purified rRNA that are specific to the 5S, 16S, or 23S subunits and extended with the enzyme reverse transcriptase. Chemical degradation or dideoxynucleotide-terminated sequencing reactions were used to determine the nucleotide sequence of the extended product. Lane et al., 82 *Proc. Natl. Acad. Sci. USA*, 6955, 1985. In a less preferred method, genomic ribosomal RNA sequences may also be determined by standard procedure.

It is not always necessary to determine the entire nucleic acid sequence in order to obtain a probe sequence. Extension from any single oligonucleotide primer can yield up to 300–400 bases of sequence. When a single primer is used to partially sequence the rRNA of the target organism and organisms closely related to the target, an alignment can be made as outlined below. If a useful probe sequence is found, it is not necessary to continue rRNA sequencing using other primers. If, on the other hand, no useful probe sequence is obtained from sequencing with a first primer, or if higher sensitivity is desired, other primers can be used to obtain more sequences. In those cases where patterns of variation for a molecule are not well understood, more sequence data may be required prior to probe design.

After sequencing, the sequences are aligned to maximize homology. The rRNA molecule has a close relationship of secondary structure to function. This imposes restrictions on evolutionary changes in the primary sequence so that the secondary structure is maintained. For example, if a base is changed on one side of a helix, a compensating change is made on the other side to preserve the complementarity (this is referred to as co-variance). This allows two very different sequences to be aligned based on the conserved primary sequence and also on the conserved secondary structure elements. Once sequences are aligned it is possible to find the regions in which the primary sequence is variable.

We have identified variable regions by comparative analysis of rRNA sequences both published in the literature and sequences which we have determined. Computers and computer programs which may be used or adapted for the purposes herein disclosed are commercially available. Since the sequence evolution at each of the variable regions (for example, spanning a minimum of 10 nucleotides) is, for the most part, divergent, not convergent, we can confidently design probes based on a few rRNA sequences which differ between the target organism and its phylogenetically closest relatives. We have seen sufficient variation between the target organism and the closest phylogenetic relative found in the same sample to design the probe of interest.

We have identified the following useful guidelines for designing probes with desired characteristics. Because the extent and specificity of hybridization reactions such as those described herein are affected by a number of factors, manipulation of one or more of those factors will determine the exact sensitivity and specificity of a particular probe, whether perfectly complementary to its target or not. The importance and effect of various assay conditions, explained further herein, are known to those skilled in the art.

First, the stability of the probe:target nucleic acid hybrid should be chosen to be compatible with the assay conditions. This may be accomplished by avoiding long A and T rich sequences, by terminating the hybrids with G:C base pairs, and by designing the probe with an appropriate Tm. The beginning and end points of the probe should be chosen so that the length and %G and %C result in a Tm about 2°–10° C. higher than the temperature at which the final assay will be performed. The base composition of the probe is significant because G-C base pairs exhibit greater thermal stability as compared to A-T base pairs due to additional hydrogen bonding. Thus, hybridization involving complementary nucleic acids of higher G-C content will be stable at higher temperatures.

Conditions such as ionic strength and incubation temperature under which a probe will be used should also be taken into account in constructing a probe. It is known that hybridization will increase as the ionic strength of the reaction mixture increases, and that the thermal stability of hybrids will increase with increasing ionic strength. On the other hand, chemical reagents, such as formamide, urea, DMSO and alcohols, which disrupt hydrogen bonds, will increase the stringency of hybridization. Destabilization of the hydrogen bonds by such reagents can greatly reduce the Tm. In general, optimal hybridization for synthetic oligonucleotide probes of about 10–50 bases in length occurs approximately 5° C. below the melting temperature for a given duplex. Incubation at temperatures below the optimum may allow mismatched base sequences to hybridize and can therefore result in reduced specificity.

It is desirable to have probes which hybridize only under conditions of high stringency. Under high stringency conditions only highly complementary nucleic acid hybrids will form (i.e., those having at least about 14 out of 17 bases in a contiguous series of bases being complementary); hybrids without a sufficient degree of complementarity will not form. Accordingly, the stringency of the assay conditions determines the amount of complementarity needed between two nucleic acid strands forming a hybrid. Stringency is chosen to maximize the difference in stability between the hybrid formed with the target and the nontarget nucleic acid.

Second, probes should be positioned so as to minimize the stability of the probe:nontarget nucleic acid hybrid. This may be accomplished by minimizing the length of perfect complementarity to non-target organisms, avoiding G and C rich regions of homology to non-target sequences, and by positioning the probe to span as many destabilizing mismatches as possible. Whether a probe sequence is useful to detect only a specific type of organism depends largely on the thermal stability difference between probe:target hybrids and probe:nontarget hybrids. In designing probes, the differences in these Tm values should be as large as possible (e.g., at least 2° C. and preferably 5° C.).

The length of the target nucleic acid sequence and, accordingly, the length of the probe sequence can also be important. In some cases, there may be several sequences from a particular region, varying in location and length, which will yield probes with the desired hybridization characteristics. In other cases, one sequence may be significantly better than another which differs merely by a single base. While it is possible for nucleic acids that are not perfectly complementary to hybridize, the longest stretch of perfectly homologous base sequence will normally primarily determine hybrid stability. While oligonucleotide probes of different lengths and base composition may be used, oligonucleotide probes preferred in this invention are between about 10 to 50 bases in length and are sufficiently homologous to the target nucleic acid.

Third, regions of the rRNA which are known to form strong internal structures inhibitory to hybridization are less preferred. Likewise, probes with extensive self-complementarity should be avoided.

As explained above, hybridization is the association of two single strands of complementary nucleic acid to form a hydrogen bonded double strand. It is implicit that if one of the two strands is wholly or partially involved in a hybrid that it will be less able to participate in formation of a new hybrid. In the case of rRNA, the molecule is known to form very stable intramolecular hybrids. By designing a probe so that a substantial portion of the sequence of interest is single stranded, the rate and extent of hybridization may be greatly increased. If the target is the genomic sequence corresponding to the rRNA then it will naturally occur in a double stranded form, this is also the case with the product of the polymerase chain reaction (PCR). These double stranded targets are naturally inhibitory to hybridization with a probe. Finally, there can be intramolecular and intermolecular hybrids formed within a probe if there is sufficient self complementarity. Such structures can be avoided through careful probe design. Computer programs are available to search for this type of interaction.

Once a presumptive unique sequence has been identified, a complementary DNA oligonucleotide is produced. This single stranded oligonucleotide will serve as the probe in the hybridization reaction. Defined oligonucleotides may be produced by any of several well known methods, including automated solid-phase chemical synthesis using cyanoethylphosphoramidite precursors. Barone et al., 12 *Nucleic Acids Research* 4051, 1984. Other well-known methods for construction of synthetic oligonucleotides may, of course, be employed. 2 J. Sambrook, E. F. Fritsch and T. Maniatis, *Molecular Cloning* 11 (2d ed. 1989).

Once synthesized, selected oligonucleotide probes may also be labelled by any of several well known methods. 2 J. Sambrook, E. F. Fritsch and T. Maniatis, *Molecular Cloning* 11 (2d ed. 1989). Useful labels include radioisotopes as well as non-radioactive reporting groups. Isotopic labels include $^3H$, $^{35}S$, $^{32}P$, $^{125}I$, 57Co and $^{14}C$. Most methods of isotopic labelling involve the use of enzymes and include the known methods of nick translation, end labelling, second strand synthesis, and reverse transcription. When using radio-labelled probes, hybridization can be detected by autoradiography, scintillation counting, or gamma counting.

The detection method selected will depend upon the hybridization conditions and the particular radioisotope used for labelling.

Non-isotopic materials can also be used for labelling, and may be introduced internally into the sequence or at the end of the sequence. Modified nucleotides may be incorporated enzymatically or chemically and chemical modifications of the probe may be performed during or after synthesis of the probe, for example, by the use of non-nucleotide linker groups. Non-isotopic labels include fluorescent molecules, chemiluminescent molecules, enzymes, cofactors, enzyme substrates, haptens or other ligands. We currently prefer to use acridinium esters.

Following synthesis and purification of a particular oligonucleotide sequence, several procedures may be utilized to determine the acceptability of the final product. The first is polyacrylamide gel electrophoresis, which is used to determine size. 2 J. Sambrook, E. F. Fritsch and T. Maniatis, *Molecular Cloning*, 11.51 (2d ed. 1989). Such procedures are known in the art. In addition to polyacrylamide gel electrophoresis, High Pressure Liquid Chromatography ("HPLC") procedures also may be used to determine the size and purity of the oligonucleotide product. These procedures are also known to those skilled in the art.

It will be appreciated by those skilled in the art that factors which affect the thermal stability can affect probe specificity and therefore, must be controlled. Thus, the melting profile, including the melting temperature (Tm) of the oligonucleotide/target hybrids should be determined. The preferred method is described in Arnold et al., patent application Ser. No. 613,603 filed Nov. 8, 1990, entitled "Homogeneous Protection Assay," assigned to Gen-Probe Incorporated, Mar. 6, 1992, Reel/Frame 6057/0433-34, hereby incorporated by reference herein, also published under European Patent Application Publication Number 0 309 230, Mar. 29, 1989.

For Tm measurement using a Hybridization Protection Assay (HPA) the following technique is used. A probe:target hybrid is formed in target excess in a lithium succinate buffered solution containing lithium lauryl sulfate. Aliquots of this hybrid are diluted in the hybridization buffer and incubated for five minutes at various temperatures starting below that of the anticipated Tm (typically 55° C.) and increasing in 2–5 degree increments. This solution is then diluted with a mildly alkaline borate buffer and incubated at a lower temperature (for example 50° C.) for ten minutes. Under these conditions the acridinium ester attached to a single stranded probe is hydrolyzed while that attached to hybridized probe is relatively protected from hydrolysis. The amount of chemiluminescence remaining is proportional to the amount of hybrid, and is measured in a luminometer by addition of hydrogen peroxide followed by alkali. The data is plotted as percent of maximum signal (usually from the lowest temperature) versus temperature. The Tm is defined as the point at which 50% of the maximum signal remains.

In addition to the above method, oligonucleotide/target hybrid melting temperature may also be determined by isotopic methods well known to those skilled in the art. It should be noted that the Tm for a given hybrid will vary depending on the hybridization solution being used because the thermal stability depends upon the concentration of different salts, detergents, and other solutes which effect relative hybrid stability during thermal denaturation. 2 J. Sambrook, E. F. Fritsch and T. Maniatis, *Molecular Cloning*, 9.51 (2d ed. 1989).

Rate of hybridization may be measured by determining the $C_0t_{1/2}$. The rate at which a probe hybridizes to its target is a measure of the thermal stability of the target secondary structure in the probe region. The standard measurement of hybridization rate is the $C_0t_{1/2}$ which is measured as moles of nucleotide per liter times seconds. Thus, it is the concentration of probe times the time at which 50% of maximal hybridization occurs at that concentration. This value is determined by hybridizing various amounts of probe to a constant amount of hybrid for a fixed time. For example, 0.05 pmol of target is incubated with 0.012, 0.025, 0.05, 0.1 and 0.2 pmol of probe for 30 minutes. The amount of hybrid after 30 minutes is measured by HPA as described above. The signal is then plotted as a log of the percent of maximum Relative Light Units (RLU) (from the highest probe concentration) versus probe concentration (moles of nucleotide per liter). RLU are a measurement of the quantity of photons emitted by the labelled-probe measured by the luminometer. The $C_0t_{1/2}$ is found graphically from the concentration corresponding to 50% of maximum hybridization multiplied by the hybridization time in seconds. These values range from $9.0 \times 10^{-6}$ to $9 \times 10^{-5}$ with the preferred values being less than $3.5 \times 10^{-5}$.

As described by Kohne and Kacian (U.S. Ser. No. 816,711, entitled "Accelerated Nucleic Acid Reassociation Method," filed Jan. 7, 1986 abandoned in favor of U.S. application Ser. No. 644,879, filed Jan. 23, 1991, issued as U.S. Pat. No. 5,132,207 on Jul. 21, 1992, hereby incorporated by reference herein), also published under European Patent Application Publication Number 0 229 442, Jul. 22, 1987, other methods of nucleic acid reassociation can be used.

The following example sets forth synthetic probes complementary to a unique rRNA sequence, or the corresponding gone, from a target organism, *Streptococcus pneumoniae*, and their use in a hybridization assay.

EXAMPLE

A probe specific for *S. pneumoniae* was identified by sequencing with a primer complementary to the 16S rRNA. The following sequence was characterized and shown to be specific for *Streptococcus pneumoniae*, Probe 1: 5' CAAAGCCTACTATGGTTAAGCC 3' (SEQ. ID. NO. 1). The phylogenetically near neighbors *S. salivarius*, *S. agalactiae* and *S. bovis* and others were used as comparisons with the sequence of *S. pneumoniae*.

This probe is 22 bases in length and hybridizes to the 16S rRNA of *S. pneumoniae* corresponding to bases 616–638 of *E. coli*. To demonstrate the reactivity and specificity of the probe for *S. pneumoniae*, it was used in a hybridization assay. The probe was first synthesized with a non-nucleotide linker, then labelled with a chemiluminescent acridinium ester as described in EPO Patent Application No. PCT/US88/03361, entitled "Acridinium Ester Labeling and Purification of Nucleotide Probes" filed Oct. 5, 1988. The acridinium ester attached to unhybridized probe is rendered non-chemiluminescent under mild alkaline conditions, while the acridinium ester attached to hybridized probe is relatively resistant. Thus, it is possible to assay for hybridization of acridinium ester-labelled probe by incubation with an alkaline buffer, followed by detection of chemiluminescence in a luminometer. Results are given in RLU, the quantity of photons emitted by the labelled-probe measured by the luminometer. The conditions of hybridization, hydrolysis and detection are described in Arnold, et al., 35 *Clin. Chem.* 1588, 1989.

Nucleic acid hybridization was enhanced by the use of "Helper Probes" as disclosed in Hogan et al., U.S. Pat. No. 5,037,557, entitled "Means and Methods for Enhancing Nucleic Acid Hybridization", and hereby incorporated by reference herein. RNA was hybridized to the acridinium ester-labeled probe in the presence of unlabeled Helper Probes, oligonucleotide SEQ. ID. NO. 2 with the sequence of 5' ACAGCCTTTAACTTCAGACTTATCTAAC-CGCCTGCGC 3' and oligonucleotide SEQ. ID. NO. 3 with the sequence of 5' TCTCCCCTCTTGCACTCAAGT-TAAACAGTTTC 3'.

In the following experiment, RNA released from one colony or $>10^8$ organisms was assayed. An example of such a method is provided by Murphy et al., U.S. Ser. No. 841,860, entitled "Method for Releasing RNA and DNA from Cells", filed Mar. 20, 1986, abandoned in favor of U.S. Ser. No. 298,765, filed Jan. 17, 1989, abandoned in favor of U.S. Ser. No. 711,114, filed Jun. 21, 1991, now U.S. Pat. No. 5,374,522 assigned to Gen-Probe Incorporated, May 23, 1986, Reel/Frame 4566/0901 hereby incorporated by reference herein, also published under European Patent Application Publication Number 0 288 618, Feb. 11, 1988. An RLU value greater than 30,000 RLU is a positive reaction; less than 30,000 is a negative reaction.

The following data show that the probes did not cross react with organisms from a wide phylogenetic cross section. These ATCC isolates were tested in duplicate, the RLU given is the average of the duplicates.

|    | ATCC NO. | ORGANISM                             | AVE RLU |
|----|----------|--------------------------------------|---------|
| 1  | 33604    | *Acinetobacter calcoaceticus*        | 876     |
| 2  | 15309    | *Acinetobacter lwoffii*              | 1016    |
| 3  | 19411    | *Actinomyces pyogenes*               | 1083    |
| 4  | 11563    | *Aerococcus viridans*                | 479     |
| 5  | 7966     | *Aeromonas hydrophila*               | 13764   |
| 6  | 27061    | *Alcaligenes denitrificans xylosoxydans* | 532 |
| 7  | 8750     | *Alcaligenes faecalis*               | 831     |
| 8  | 6051     | *Bacillus subtilis*                  | 946     |
| 9  | 23745    | *Bacteroides fragilis*               | 33964   |
| 10 | 10580    | *Bordetella bronchiseptica*          | 585     |
| 11 | 25238    | *Branhamella catarrhalis*            | 7590    |
| 12 | 9172     | *Brevibacterium linens*              | 753     |
| 13 | 33560    | *Campylobacter jejuni*               | 547     |
| 14 | 18804    | *Candida albicans*                   | 620     |
| 15 | 27872    | *Capnocytophaga ochracea*            | 470     |
| 16 | 29094    | *Chromobacterium violaceum*          | 3176    |
| 17 | 14501    | *Clostridium innocuum*               | 630     |
| 18 | 13124    | *Clostridium perfringens*            | 1753    |
| 19 | 11913    | *Corynebacterium diptheriae*         | 530     |
| 20 | 9345     | *Corynebacterium haemolyticum*       | 1471    |
| 21 | 10700    | *Corynebacterium pseudodiphtheriticum* | 546   |
| 22 | 19410    | *Corynebacterium pseudotuberculosis* | 605     |
| 23 | 373      | *Corynebacterium xerosis*            | 570     |
| 24 | 32045    | *Cryptococcus neoformans*            | 730     |
| 25 | 35073    | *Deinococcus radiodurans*            | 11632   |
| 26 | 15994    | *Derxia gummosa*                     | 7931    |
| 27 | 14025    | *Enterococcus avium*                 | 734     |
| 28 | 19433    | *Enterococcus faecalis*              | 526     |
| 29 | 18434    | *Enterococcus faecium*               | 779     |
| 30 | 19414    | *Erysipelothrix rhusiopathiae*       | 657     |
| 31 | 10798    | *Escherichia coli*                   | 808     |
| 32 | 13253    | *Flavobacterium meningosepticum*     | 9435    |
| 33 | 10379    | *Gemella haemolysans*                | 2115    |
| 34 | 19418    | *Haemophilus influenzae*             | 2013    |
| 35 | 23357    | *Klebsiella pneumoniae*              | 2119    |
| 36 | 4356     | *Lactobacillus acidophilus*          | 766     |
| 37 | 19257    | *Lactococcus lactis cremoris*        | 554     |
| 38 | 33152    | *Legionella pneumophila*             | 1259    |
| 39 | 33313    | *Leuconostoc paramesenteroides*      | 656     |
| 40 | 35152    | *Listeria monocytogenes*             | 628     |
| 41 | 27570    | *Micrococcus kristinae*              | 638     |
| 42 | 4698     | *Micrococcus luteus*                 | 700     |

| ATCC NO. | ORGANISM | AVE RLU |
|---|---|---|
| 43 | 14470 | Mycobacterium gordonae | 527 |
| 44 | 25177 | Mycobacterium tuberculosis | 458 |
| 45 | 14027 | Mycoplasma hominis | 459 |
| 46 | 15531 | Mycoplasma pneumoniae | 464 |
| 47 | 13077 | Neisseria meningitidis | 2731 |
| 48 | 19247 | Nocardia asteroides | 1624 |
| 49 | 33225 | Oerskovia turbata | 21312 |
| 50 | 27402 | Oerskovia xanthineolytica | 1010 |
| 51 | 17741 | Paracoccus denitrificans | 970 |
| 52 | 33314 | Pediococcus acidilactici | 572 |
| 53 | 27337 | Peptostreptococcus anaerobius | 535 |
| 54 | 6919 | Propionibacterium acnes | 470 |
| 55 | 25933 | Proteus mirabilis | 8221 |
| 56 | 25330 | Pseudomonas aeruginosa | 2220 |
| 57 | 33071 | Rahnella aquatilis | 1170 |
| 58 | 25592 | Rhodococcus bronchialis | 809 |
| 59 | 11170 | Rhodospirillum rubrum | 1310 |
| 60 | 12598 | Staphylococcus aureus | 661 |
| 61 | 33591 | Staphylococcus aureus | 639 |
| 62 | 25923 | Staphylococcus aureus | 483 |
| 63 | 12228 | Staphylococcus epidermidis | 580 |
| 64 | 13813 | Streptococcus agalactiae | 568 |
| 65 | 33397 | Streptococcus anginosus | 1022 |
| 66 | 33317 | Streptococcus bovis | 743 |
| 67 | 27823 | Streptococcus constellatus | 1120 |
| 68 | 27957 | Streptococcus dysgalactiae | 11846 |
| 69 | 9812 | Streptococcus equinus | 679 |
| 70 | 9811 | Streptococcus mitis | 920 |
| 71 | 6249 | Streptococcus mitis | 703 |
| 72 | 43205 | Streptococcus mitis | 664 |
| 73 | 15911 | Streptococcus mitis | 640 |
| 74 | 27824 | Streptococcus morbillorum | 1049 |
| 75 | 25175 | Streptococcus mutans | 503 |
| 76 | 6303 | Streptococcus pneumoniae | 607981 |
| 77 | 35088 | Streptococcus pneumoniae | 456371 |
| 78 | 6314 | Streptococcus pneumoniae | 393539 |
| 79 | 6306 | Streptococcus pneumoniae | 324262 |
| 80 | 33400 | Streptococcus pneumoniae | 244720 |
| 81 | 19615 | Streptococcus pyogenes | 2215 |
| 82 | 13419 | Streptococcus salivarius | 467 |
| 83 | 15909 | Streptococcus sanguis | 1793 |
| 84 | 10557 | Streptococcus sanguis | 963 |
| 85 | 9342 | Streptococcus species Group C | 4700 |
| 86 | 12388 | Streptococcus species Group C | 1645 |
| 87 | 12392 | Streptococcus species Group F2 | 2105 |
| 88 | 12394 | Streptococcus species Group G | 4160 |
| 89 | 27958 | Streptococcus uberis | 464 |
| 90 | 23345 | Streptomyces griseus | 607 |
| 91 | 17802 | Vibrio parahaemolyticus | 12317 |
| 92 | 9610 | Yersinia enterocolitica | 1189 |

The above data confirm that the novel probes herein disclosed and claimed are capable of distinguishing *Streptococcus pneumoniae* from its known nearest phylogenetic neighbors.

Other embodiments are within the following claims.

I claim:

1. A nucleic acid hybridization assay probe up to 100 nucleotides in length comprising a nucleotide base sequence sufficiently complementary to hybridize to a *Streptococcus pneumoniae* nucleic acid target region to form a detectable target:probe hybrid under high stringency hybridization assay conditions, said target region corresponding to, or perfectly complementary to a nucleic acid corresponding to, the nucleotide position 616–638 of *E. coli* 16S rRNA, wherein under said conditions said probe does not hybridize to nucleic acid from *Streptococcus salivarius*, *Streptococcus agalactiae* or *Streptococcus bovis*, to form a detectable probe:non-target hybrid.

2. A nucleic acid hybridization assay probe 15 to 100 bases in length comprising an oligonucleotide which hybridizes to a *Streptococcus pneumoniae* nucleic acid target region to form a detectable target:probe hybrid under high stringency hybridization assay conditions, said oligonucleotide comprising at least 14 out of 17 consecutive bases complementary to a target sequence present in said target region, said target region corresponding to, or perfectly complementary to a nucleic acid corresponding to, the nucleotide position 616–638 of *E. coli* 16S rRNA, wherein said probe does not hybridize to nucleic acid from *Streptococcus salivarius*, *Streptococcus agalactiae* or *Streptococcus bovis*, to form a detectable probe:non-target hybrid under said conditions.

3. The probe of claim 2, wherein said oligonucleotide comprises 17 out of 17 contiguous nucleotides perfectly complementary to said target sequence.

4. The probe of claim 2, wherein said oligonucleotide comprises a nucleic acid sequence selected from the group consisting of:

5' CAAAGCCTACTATGGTTAAGCC (SEQ ID NO: 1),
5' CAAAGCCUACUAUGGUUAAGCC (SEQ ID NO: 4),
5' GGCTTAACCATAGTAGGCTTTG (SEQ ID NO: 5), and
5' GGCUUAACCAUAGUAGGCUUUG (SEQ ID NO: 6).

5. The probe of claim 4, wherein said probe is 22–50 nucleotides in length.

6. The probe of claim 5, wherein said oligonucleotide consists of said nucleic acid sequence.

7. The probe of claim 6, wherein said oligonucleotide is labeled with a detectable moiety.

8. The probe of claim 7, wherein said detectable moiety is selected from the group consisting of: radioisotope, chemiluminescent molecule, fluorescent molecule, enzyme, cofactor, enzyme substrate, and hapten.

9. The probe of claim 8, wherein said detectable moiety is an acridinium ester.

10. A nucleic acid hybrid comprising:

a) a nucleic acid hybridization assay probe 15 to 100 bases in length comprising an oligonucleotide which hybridizes to a *Streptococcus pneumoniae* nucleic acid target region corresponding to, or perfectly complementary to a nucleic acid corresponding to, the nucleotide position 616–638 of *E. coli* 16S rRNA, to form a detectable target:probe hybrid under high stringency hybridization assay conditions, said oligonucleotide comprising at least 14 out of 17 consecutive bases complementary to a target sequence present in said target region, wherein said target region has a sequence selected from the group consisting of; 5' CAAAGCCTACTATGGT-TAAGCC (SEQ ID NO: 1), and 5' GGCUUAAC-CAUAGUAGGCUUUG (SEQ ID NO: 6);

wherein said probe does not hybridize to nucleic acid from Streptococcus salivarius, Streptococcus agalactiae or Streptococcus bovis, to form a detectable probe:non-target hybrid under said conditions; and b) Streptococcus pneumoniae nucleic acid comprising nucleic acid corresponding to the nucleotide position 616–638 of E. coli 16S rRNA or rDNA.

11. The nucleic acid hybrid of claim 10, wherein said probe is 22 to 50 nucleotides in length and comprises a nucleic acid sequence selected from the group consisting of:
5' CAAAGCCTACTATGGTTAAGCC (SEQ ID NO: 1),
5' CAAAGCCUACUAUGGUUAAGCC (SEQ IU NO: 4),
5' GGCTTAACCATAGTAGGCTTTG (SEQ ID NO: 5), and
5' GGCUUAACCAUAGUAGGCUUUG (SEQ ID NO: 6).

12. The nucleic acid hybrid of claim 11, wherein said oligonucleotide consists of said nucleic acid sequence.

13. A probe mix comprising:

a) a nucleic acid hybridization assay probe 15 to 100 bases in length comprising an oligonucleotide which hybridizes to a Streptococcus pneumoniae nucleic acid target region to form a detectable target:probe hybrid under high stringency hybridization assay conditions, said target region corresponding to, or perfectly complementary to a nucleic acid corresponding to, the nucleotide position 616–638 of E. coli 16S rRNA, wherein said oligonucleotide comprises a sequence of 14 out of 17 consecutive bases complementary to a hybridization assay probe target sequence selected from the group consisting of; 5' CAAAGCCTACTATGGTTAAGCC (SEQ ID NO: 1), and 5' GGCUUAACCAUAGUAG-GCUUUG (SEQ ID NO: 6), wherein said probe does not hybridize to nucleic acid from Streptococcus salivarius, streptococcus agalactiae or Streptococcus bovis, to form a detectable probe:non-target hybrid under said conditions; and b) a helper probe comprising a sequence selected from the group consisting of: SEQ ID No: 2: ACAGCCTTTA ACTTCAGACT TATCTAACCG CCTGCGC, SEQ ID No: 3: TCTCCCCTCT TGCACTCAAG TTAAA-CAGTT TC, and the sequences perfectly complementary thereto.

14. The probe mix of claim 13, wherein said oligonucleotide has at least 14 out of 17 consecutive bases perfectly complementary to 5' GGCUUAACCAUAGUAGGCUUUG (SEQ ID NO: 6); and said helper probe comprises a helper probe sequence selected from the group consisting of:
SEQ ID No: 2: ACAGCCTTTA ACTTCAGACT TATCTAACCG CCTGCGC; and
SEQ ID No: 3: TCTCCCCTCT TGCACTCAAG TTAAA-CAGTT TC.

15. The probe mix of claim 14, wherein said hybridization assay probe sequence comprises the hybridization assay probe sequence 5' CAAAGCCTACTATGGTTAAGCC (SEQ ID NO: 1).

16. The probe mix of claim 15, wherein said hybridization assay probe consists of said hybridization assay probe sequence and said helper probe consists of said helper probe sequence.

17. A method for determining whether Streptococcus pneumoniae may be present in a sample comprising the steps of:

a) providing to said sample a nucleic acid hybridization assay probe comprising a nucleotide base sequence region which hybridizes to a Streptococcus pneumoniae nucleic acid target region to form a detectable target:probe hybrid under high stringency hybridization assay conditions, said nucleotide base sequence region comprising at least 14 out of 17 consecutive bases complementary to a target sequence present in said target region, said target region corresponding to, or perfectly complementary to a nucleic acid corresponding to, the nucleotide position 616–638 of E. coli 16S rRNA, wherein said probe does not hybridize to nucleic acid from Streptococcus salivarius, Streptococcus agalactiae or Streptococcus bovis, to form a detectable probe:non-target hybrid under said conditions, and b) detecting whether said probe hybridizes to nucleic acid present in said sample under said hybridization conditions as an indication that Streptococcus pneumoniae may be present in said sample.

18. The method of claim 17, wherein said oligonucleotide comprises 17 out of 17 contiguous nucleotides perfectly complementary to said target sequence.

19. The method of claim 17, wherein said probe comprises a nucleic acid sequence selected from the group consisting of:
5' CAAAGCCTACTATGGTTAAGCC (SEQ ID NO: 1),
5' CAAAGCCUACUAUGGUUAAGCC (SEQ ID NO: 4),
5' GGCTTAACCATAGTAGGCTTTG (SEQ ID NO: 5), and
5' GGCUUAACCAUAGUAGGCUUUG (SEQ ID NO: 6).

20. The method of claim 19, wherein said probe is 22–50 nucleotides in length.

21. A method for determining whether Streptococcus pneumoniae may be present in a sample comprising the steps of:

a) providing to said sample a nucleic acid hybridization assay probe consisting of a nucleic acid sequence selected from the group consisting of:
5' CAAAGCCTACTATGGTTAAGCC (SEQ ID NO: 1),
5' CAAAGCCUACUAUGGUUAAGCC (SEQ ID NO: 4),
5' GGCTTAACCATAGTAGGCTTTG (SEQ ID NO: 5), and
5' GGCUUAACCAUAGUAGGCUUUG (SEQ ID NO: 6); and b) detecting whether said probe hybridizes to nucleic acid present in said sample under hybridizations conditions wherein said probe does not hybridize to nucleic acid from Streptococcus salivarius, Streptococcus agalactiae or Streptococcus bovis to form a detectable probe:non-target hybrid, as an indication that Streptococcus pneumoniae may be present in said sample.

22. The method of claim 21, wherein said probe is labeled with a detectable moiety.

23. The method of claim 22, wherein said detectable moiety is selected from the group consisting of: radioisotope, chemiluminescent molecule, fluorescent molecule, enzyme, cofactor, enzyme substrate, and hapten.

24. The method of claim 23, wherein said detectable moiety is an acridinium ester.

* * * * *